(12) United States Patent
Thomas (10) Patent No.: US 11,413,416 B2
(45) Date of Patent: Aug. 16, 2022

(54) ENDOPHARYNGEAL AIRWAY POSITIVE PRESSURE VENTILATION DEVICE

(71) Applicant: Diana B. Thomas, Lexington, KY (US)

(72) Inventor: Diana B. Thomas, Lexington, KY (US)

( * ) Notice: Subject to any disclaimer, the term of this patent is extended or adjusted under 35 U.S.C. 154(b) by 293 days.

(21) Appl. No.: 16/556,112

(22) Filed: Aug. 29, 2019

(65) Prior Publication Data

US 2020/0101251 A1 Apr. 2, 2020

Related U.S. Application Data

(63) Continuation-in-part of application No. 14/756,039, filed on Jul. 23, 2015, now abandoned.

(60) Provisional application No. 61/999,314, filed on Jul. 23, 2014.

(51) Int. Cl.

| A61M 16/08 | (2006.01) |
|---|---|
| A61M 16/00 | (2006.01) |
| A61M 16/10 | (2006.01) |
| A61M 16/04 | (2006.01) |
| A61M 16/06 | (2006.01) |

(52) U.S. Cl.
CPC .... A61M 16/0461 (2013.01); A61M 16/0078 (2013.01); A61M 16/0816 (2013.01); A61M 16/104 (2013.01); A61M 16/1005 (2014.02); *A61M 16/0666* (2013.01); *A61M 2016/103* (2013.01)

(58) Field of Classification Search
CPC .. A61M 16/00; A61M 16/0078; A61M 16/04; A61M 16/0461; A61M 16/0463; A61M 16/0475; A61M 16/0484; A61M 16/0816; A61M 16/1005; A61M 16/104
See application file for complete search history.

(56) References Cited

U.S. PATENT DOCUMENTS

| 5,193,544 A | 3/1993 | Jaffe |
|---|---|---|
| 5,555,890 A | 9/1996 | Schaller |
| 5,690,620 A | 11/1997 | Knott |
| 6,098,617 A | 8/2000 | Connell |
| 6,266,547 B1 | 7/2001 | Walker |
| 6,379,312 B2 | 4/2002 | O'Toole |

(Continued)

*Primary Examiner* — Joseph D. Boecker
(74) *Attorney, Agent, or Firm* — Carrithers Law Office, PLLC; David W. Carrithers; Adam D. Carrithers (57) ABSTRACT

An endopharyngeal airway positive pressure ventilation device and method of use for ventilating a patient through a nasopharyngeal airway in surgical settings that is incapable of normal ventilation with current anesthetic techniques due to a risk for airway obstruction in surgical procedures requiring conscious sedation monitored anesthesia care (MAC). The invention includes a single-lumen endopharyngeal nasal tube with an eye shaped opening at its distal end and a cylindrical proximal end used as an adaptor for anesthetic applications such as positive airway pressure via JACKSON-REES modified ambu-bag or other various anesthesiology applications. Contiguous to the distal end of the nasal tube is an end-tidal CO2 monitoring port (ETCO2). On the distal end of the flexible nasal ventilation tube is an eye opening allowing air flow to the posterior pharynx. The device further includes a modified JACKSON-REES ambu bag which allows for controlled airflow to the patient during a REESE procedure.

3 Claims, 7 Drawing Sheets

(56) References Cited

U.S. PATENT DOCUMENTS

| | | |
|---|---|---|
| 6,789,538 B2 * | 9/2004 | Wright .............. A61M 16/0084 |
| | | 128/200.26 |
| 6,938,619 B1 | 9/2005 | Hickle |
| 7,730,888 B2 | 6/2010 | Dunlap |
| 7,832,400 B2 | 11/2010 | Curti |
| 8,413,658 B2 | 4/2013 | Williams |
| 2004/0230108 A1 | 11/2004 | Melker |
| 2004/0231675 A1 | 11/2004 | Lyons |
| 2005/0092329 A1 | 5/2005 | Sta-Maria |
| 2007/0267024 A1 | 11/2007 | Kremer |
| 2008/0303108 A1 | 12/2008 | Kasano et al. |
| 2009/0013995 A1 | 1/2009 | Williams |
| 2009/0038620 A1 | 2/2009 | Efrati |
| 2009/0151724 A1 | 6/2009 | Wondka |
| 2009/0156953 A1 | 6/2009 | Wondka |
| 2011/0009763 A1 | 1/2011 | Levitsky |
| 2011/0098592 A1 | 4/2011 | Colman |
| 2011/0178439 A1 | 7/2011 | Irwin |
| 2011/0315147 A1 | 12/2011 | Wood |
| 2012/0080037 A1 | 4/2012 | Guyuron |
| 2012/0118297 A1 | 5/2012 | Barodka |
| 2013/0019872 A1 | 1/2013 | Guyuron |
| 2013/0338521 A1 * | 12/2013 | Thompson ........ A61M 16/0484 |
| | | 600/532 |
| 2014/0309545 A1 | 10/2014 | Simon |
| 2016/0022941 A1 | 1/2016 | Ozenne |

* cited by examiner

*PRIOR ART*

FIG. 12

ENDOPHARYNGEAL AIRWAY POSITIVE PRESSURE VENTILATION DEVICE

CROSS REFERENCE TO RELATED APPLICATIONS

This is a Continuation-In-Part application claiming priority from U.S. application Ser. No. 14/756,039 filed on Jul. 23, 2015 and claims priority from U.S. Provisional Application Ser. No. 61/999,314 filed on Jul. 23, 2014 both of which are incorporated herein in its entirety.

FIELD OF THE INVENTION

The present invention pertains to an anesthetic device and device and more particularly, to a endopharyngeal airway device and device for the delivery of positive-pressure ventilation thorough a nasopharyngeal airway in surgical settings in patients at risk for airway obstruction in surgical procedures requiring conscious sedation/monitored anesthesia care (MAC).

BACKGROUND OF THE INVENTION

Historically, the traditional nasal airway provided adequate assistance in relieving partial airway obstruction. However, in patients with obstructive sleep apnea (OSA) and morbid obesity, opening an airway is often not sufficient to ventilate the patient.

Increasing risks of airway obstruction secondary to rising incidence of obstructive sleep apena (OS) and morbid obesity; and increasing number of anesthesia cases being performed in non-traditional settings (dental offices, endoscopy suites, outpatient ambulatory surgical centers (ASC) using IV sedation with PROPOFOL or PRECEDEX. In patients with OSA or morbid obesity, opening and airway is often not sufficient to adequately ventilate the patient.

More than 60% of elective surgery procedures in the U.S. are performed in outpatient setting (15,000,000 cases), which is expected to reach 75% by the end of the next decade. Forty-two percent of all outpatient surgeries take place in an ASC. The above percentage is expected to rise due to better outpatient reimbursement (over 50% covered by private insurance), and overall cost savings of outpatient procedures over inpatient. Many outpatient/ASC procedures are typically performed using MAC conscious sedation forms of anesthesia whereby shorter acting anesthetics are used to place the patient in a deep state of anesthesia and the patient is not put on a ventilator so the patient breathes by their self During MAC anesthesia procedures, air and/or oxygen is delivered to the patient through a facial masks of a nasal cannula when the mask interferes with the procedure. GI endoscopy (the most common outpatient procedure) is now mandated to be covered by all insurance.

An endotracheal tube is often fitted in the patient's trachea to administer anesthesia and a mechanical ventilator can be used to pump air and/or oxygen into the patient's lungs and extract carbon dioxide therefrom. Carbon dioxide monitors are quick to detect an interruption of ventilation.

Conventional devices adapted for use with a nasal or oral nasopharyngeal airway typically consist of a length of tube for insertion into an airway.

U.S. Publication 20130338521 by Thompson teaches a plurality of small openings in the sidewall of the tube, contrary to Applicant's claimed invention utilizing a single oblong opening in the sidewall of the tube allowing sufficient air to enter the tube to prevent collapse from clogging of the distal end. Thompson does not disclose nor suggest the proximal end of the adaptor cooperatively engages a fitting of an anesthetic application device comprising a positive airway pressure via a JACKSON-REES modified ambu-bag for providing controlled airflow to the patient during a procedure as set forth in the present invention having an endopharyngeal flexible nasal ventilation tube is of a selected size having a distal eye opening and an opening in a sidewall allowing for airflow to the posterior pharynx in the event that the distal eye is covered by body tissue and distributing positive pressure air into the airway of the patient preventing dislodging of said nasal ventilation tube form the nostril of the patient due to excessive pressure buildup in the airway.

U.S. Pat. No. 6,098,617 by Connell teaches a specialized endotracheal tube for administering and sampling inhalant and expired gases in an oro/nasopharyngeal airway tube including a connecting flange incorporating a pair of small conduits adapted to slide into an internal passage of the tube with a first delivery tube disposed in the proximate end to provide inhalant gas "O2" with the distal end of the second sample tube disposed near the distal end of airway tube to contact expired gas "CO2" when the airway is being used.

U.S. Pat. No. 6,789,538 by Wright teaches a rescue device and kit for ventilating a patient including a single-lumen nasopharyngeal nasal trumpet having a beveled shaped opening at its distal end and a flared proximal end having an eye opening disposed proximal to the beveled shaped opening.

If a patient becomes so sedated that breathing becomes slow or stops of a respiration failure is detected due to an obstruction or closure of the patient's airway, the anesthetist must restore proper breathing.

Therefore, it would be highly desired to have a new and improved method, device and device for establishing a positive pressure endopharyngeal airway without the need of providing a surgical airway.

SUMMARY OF THE INVENTION

The present invention pertains to an anesthetic device and device and more particularly, to a endopharyngeal airway device and device for the delivery of positive-pressure ventilation thorough a nasopharyngeal airway in surgical settings in patients at risk for airway obstruction in surgical procedures requiring conscious sedation/monitored anesthesia care (MAC).

Providing direct air and/or oxygen and the ability to provide positive airway pressure is needed and provided by the instant endopharyngeal device (EPA). Conventional nasopharyngeal devices used to open an obstructed nasal passage do not allow for positive airway ventilation nor the ability to monitor adequacy of ventilation via an end-tidal carbon dioxide CO2 (ETCO2).

The instant invention provides a means to provide application of controlled positive airway pressure and feedback in patients at risk for airway obstruction in surgical procedures requiring conscious sedation/monitored anesthesia care (MAC). It is recommended for MAC anesthesia with sedation in patients at risk for partially obstructed airways. It is not recommended for general anesthesia. It should be used with caution in patients taking anticoagulants, and it not recommended for patients with facial trauma including facial fractures.

The device includes a single-lumen flexible endopharyngeal nasal ventilation tube including an eye shaped opening at its distal end and an adapter having a cylindrical proximal end removable coupling to a positive airway pressure device. An end-tidal CO2 monitoring port is contiguous to the distal end of the nasal tube. An eye opening on the distal end of the endopharyngeal nasal ventilation tube allowing air flow to the posterior pharynx. A positive airway pressure device such as a JACKSON REES bag allows for controlled positive pressure airflow to the patient during a procedure.

The present invention comprises a unit containing an improved endopharyngeal airway device for ventilating a patient incapable of normal ventilation with current anesthetic techniques due to a risk for airway obstruction in surgical procedures requiring conscious sedation/monitored anesthesia care (MAC). Includes a single-lumen endopharyngeal nasal tube with an eye shaped opening spaced apart a selected distance from its tapered distal end and a cylindrical proximal end used as an adaptor for anesthetic applications such as positive airway pressure via JACKSON-REES modified ambu-bag or other various anesthesiology applications. Contiguous to the distal end of the nasal tube is an end-tidal CO2 monitoring port (ETCO2). The end-tidal CO2 monitoring port tube is partially enclosed in the proximal end of the flexible nasal ventilation tube. The flexible nasal ventilation tube is made of a latex-free, non-toxic material. On the distal end of the flexible nasal ventilation tube is an eye opening allowing air flow to the posterior pharynx. Contiguous to the distal eye opening is an opening in the sidewall of the flexible nasal ventilation tube allowing for airflow to the posterior pharynx in the event that the distal eye is covered by body tissue. The device further includes a modified JACKSON-REES ambu bag which allows for controlled airflow to the patient during a procedure. A medical practitioner using the endopharyngeal airway proceeds ventilating a patient by using neosynephrine nasal spray in the least obstructed nare, selecting a flexible nasal ventilation tube size by measuring from the tip of the nose to the earlobe or angle of jaw, applying lubricating gel to the flexible nasal ventilation tube, and inserting the flexible nasal ventilation tube into the nares with a gentle rotating motion. When the flexible nasal ventilation tube is in the correct position, it will extend from the distal end of the tube to the posterior of the pharynx.

A medical practitioner using the endopharyngeal airway proceeds by ventilating a patient using neosynephrine nasal spray in the least obstructed nare, selecting a flexible nasal ventilation tube size by measuring from the tip of the nose to the earlobe or angle of jaw, applying lubricating gel to the flexible nasal ventilation tube, and inserting the flexible nasal ventilation tube into the nares with a gentle rotating motion. When the flexible nasal ventilation tube is in the correct position, it will extend from the distal end of the tube to the posterior of the pharynx. With the nasal tube so positioned the medical practitioner applies positive pressure to the modified JACKSON-REES ambu bag in synchronization with the inspiratory phase allowing sufficient time for exhalation through the mouth of the patient.

The tube size is selected by measuring from tip of the nose to earlobe or angle of the jaw. Lubricating gel is applied to the tube. The tube is inserted into the nare with gentle rotating motion. When the tube is in the correct position it will extend from the nare to the posterior pharynx. It does not extend down pass the tracheae.

It is an objective of the present invention to utilize a flexible tube made of latex free nontoxic material.

It is an objective of the present invention to provide an end-tidal carbon dioxide monitoring port (ETCO2).

It is an objective of the present invention to provide an coupling having a endopharyngeal nasal tube adaptor having a distal male end nipple for removable cooperative engagement with a proximate end of a flexible endopharyngeal nasal tube and a tube extending from a tidal CO2 monitoring port and having an opposing male end in removable cooperative engagement with a sleeve of the universal adapter removably connecting to a JACKSON-REES ambu-bag and having a tee stem connecting to a ventilation pump tube.

It is an objective of the present invention to provide a distal eye to provide more efficient and controlled flow of air to posterior pharynx especially in case the opening in the distal end of the tube is partially blocked by tissue or other obstruction.

It is an objective of the present invention to provide an adaptor for anesthesia applications such as positive airway pressure via JACKSON-REES modified ambu-bag or ventilator.

It is an objective of the present invention to provide means for administering a neosynephrine nasal spray in one of the least obstructed nares.

It is an objective of the present invention to provide for an ETCO2 port for continuous monitoring of carbon dioxide providing feedback to enable control of the amount of air to the patient.

It is another objective of the present invention top provide for a distal eye in the airway tube to improve airway patency.

It is an objective of the present invention to provide an adaptor for possible anesthesia applications including direct air and/or oxygen delivery to posterior pharynx; non-rebreather bay with pressure relief valve for positive airway pressure; JACKSON-REES modified ambu-bag and anesthesia circuit with PSV pro for portable spontaneous ventilation with pressure support.

The use of an eye, use of carbon dioxide port or which can be integrally molded as part of the connection or "adapter" which uses a universal friction fit coupling on the end of a tube which cooperatively engages the air bag provides an inexpensive means for providing direct air and/or oxygen and the ability to provide positive airway pressure is needed.

Other objects, features, and advantages of the invention will be apparent with the following detailed description taken in conjunction with the accompanying drawings showing a preferred embodiment of the invention.

BRIEF DESCRIPTION OF THE DRAWINGS

A better understanding of the present invention will be had upon reference to the following description in conjunction with the accompanying drawings in which like numerals refer to like parts throughout the views wherein.

DETAILED DESCRIPTION OF THE PREFERRED EMBODIMENT

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly. References to "front," "back," "rear," "upper," "lower," "right," and "left" are used to identify the various elements to a user facing the sink, and with "lateral" being left-right.

It should further be noted that for purposes of this disclosure, the term coupled means the joining of two members directly or indirectly to one another. Such joining may be stationary in nature or moveable in nature and/or such joining may allow for the flow of fluids, electricity, electrical signals, or other types of signals or communication between the two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

As used herein, the term "about" can be reasonably appreciated by a person skilled in the art to denote somewhat above or somewhat below the stated numerical value, to within a range of ±10%.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The endopharyngeal airway unit provides for controlled delivery of positive-pressure ventilation thorough a nasopharyngeal airway in surgical settings in patients at risk for airway obstruction in surgical procedures requiring conscious sedation/monitored anesthesia care (MAC) with feedback to allow monitoring and controlled amounts of pressurized air to the patient for ventilating a patient incapable of normal ventilation with current anesthetic techniques due to a risk for airway obstruction in surgical procedures requiring conscious sedation/monitored anesthesia care (MAC). A single-lumen endopharyngeal nasal tube with an eye shaped opening spaced apart a selected distance from its tapered distal end and a cylindrical proximal end forms an adaptor for anesthetic applications for removably coupling to a positive airway pressure via JACKSON-REES modified ambu-bag or other anesthesiological device. The cylindrical, proximal end of the nasal tube is adapted to be removably connected in a fast, convenient manner to an air delivery device. Contiguous to the proximate end of the nasal tube is an end-tidal $CO_2$ monitoring port (ETCO2). The end-tidal $CO_2$ monitoring port is enclosed in the proximal end of the flexible nasal ventilation tube. The flexible nasal ventilation tube is made of a latex-free, non-toxic material. Spaced apart a selected distance from the distal end of the flexible nasal ventilation tube is an eye opening allowing air flow to the posterior pharynx. The distal eye opening in the sidewall of the flexible nasal ventilation tube allows for airflow to the posterior pharynx in the event that the distal eye is covered by body tissue. The unit typically includes a modified JACKSON-REES ambu bag which allows for controlled airflow to the patient during a surgical procedure.

Referring now to the drawings and more particularly to FIGS. 1-12, thereof there is illustrated a respiratory ventilation device 8, which is constructed in accordance with one preferred embodiment of the present invention. The respiratory ventilation device 8 is utilized to ventilate a patient incapable of normal ventilation with current anesthetic techniques due to a risk for airway obstruction in surgical procedures requiring conscious sedation/monitored anesthesia care (MAC).

Figure 1:
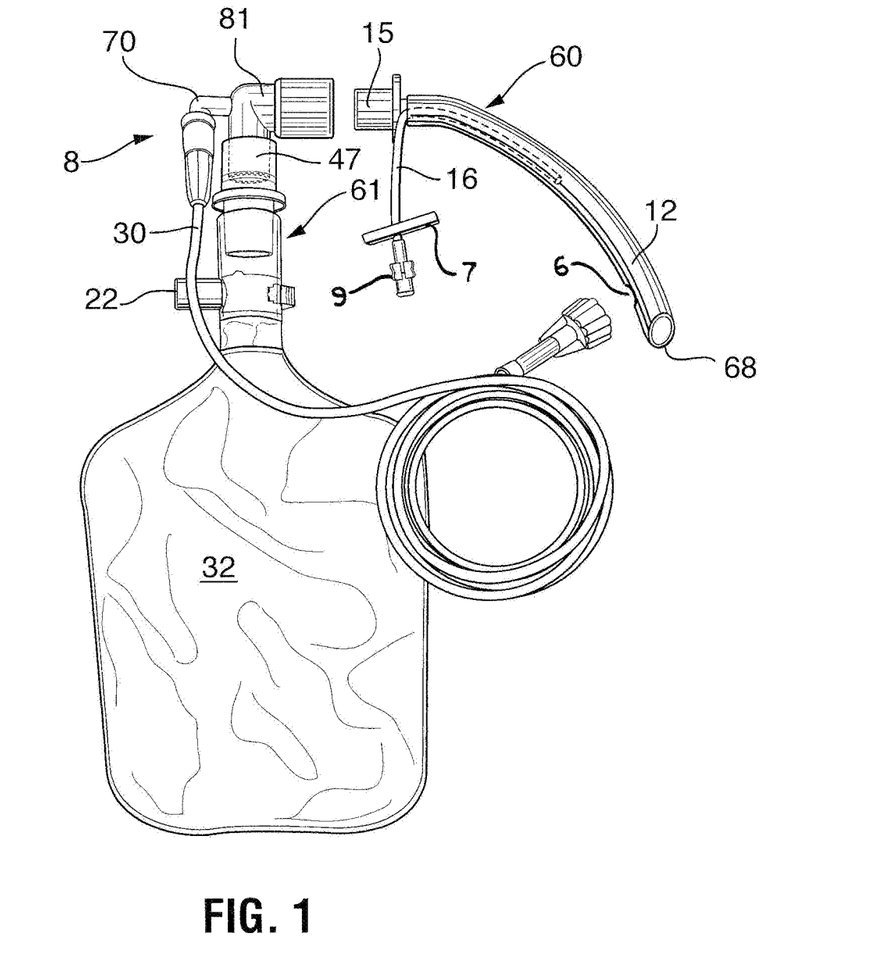
FIG. 1 is a perspective view of the completely assembled device showing the distal end of the nasal tube and proximal end of the end-tidal CO2 monitor port enclosed by the flexible nasal ventilation tube with the modified JACKSON-REES ambu bag detached from the adaptor.

As illustrated in FIG. 1, the completely assembled device showing the distal end of the nasal tube and proximal end of the end-tidal $CO_2$ monitor port enclosed by the flexible nasal ventilation tube with the modified JACKSON-REES ambu bag detached from the adaptor, illustrating how the adaptor for various anesthesiology applications attaches to the modified JACKSON-REES ambu bag with the nipple in flow communication with a sleeve valve, and an air delivery system via ventilation pump tube.

The respiratory ventilation device 8 generally comprises an air delivery assembly 61 and a single-lumen endopharyngeal nasal tube 60 with an eye shaped opening 6 at its distal end 63 and a cylindrical proximal end or male fitting part of the endopharyngeal nasal tube adaptor 15 of the endopharyngeal nasal tube 60. Contiguous to the distal end of the nasal tube 60 is an end-tidal $CO_2$ monitoring port 9 (ETCO2) connecting to tube 16 and a clamp 7 for shutting off the tube 16. The distal end of the nasal tube 60 and proximal end of the end-tidal $CO_2$ monitoring port 16 are enclosed in the proximal end of the flexible nasal ventilation tube 12. The flexible nasal ventilation tube 12 is made of a latex-free, non-toxic material.

Figure 5:
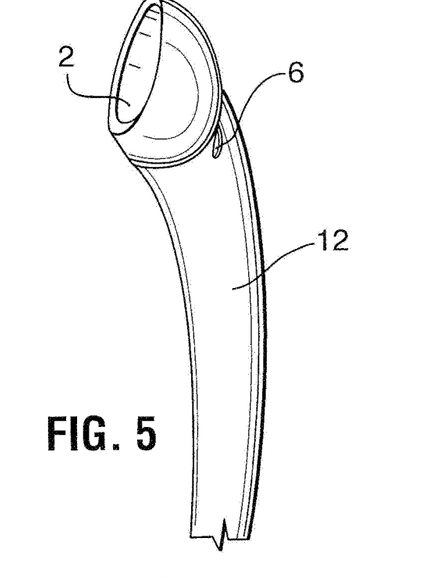
FIG. 5 is a perspective view of the eye opening at the distal end of the flexible nasal ventilation tube and the distal eye posterior to the pharynx contiguous with it.

On the distal end of the flexible nasal ventilation tube 12 is an eye opening 2 allowing air flow to the posterior pharynx. Contiguous to the distal eye opening 2 is an opening in the sidewall 6 of the flexible nasal ventilation tube 12 allowing for airflow to the posterior pharynx in the event that the distal eye is covered by body tissue. The opening in the sidewall 6 in cooperation with the distal eye opening 2 helps distribute positive pressure air into the airway of a patient and thus, helps prevent the tube 60 from being dislodged from the nostril of the patient due to excessive pressure buildup in the airway of the patient. In this manner the delivery of the positive pressure air into the airway of the patient causes the periglottic area within the airway to expand or distend and causes the larynx to open, thus facilitating the pulmonary exchange of air.

Figure 2:
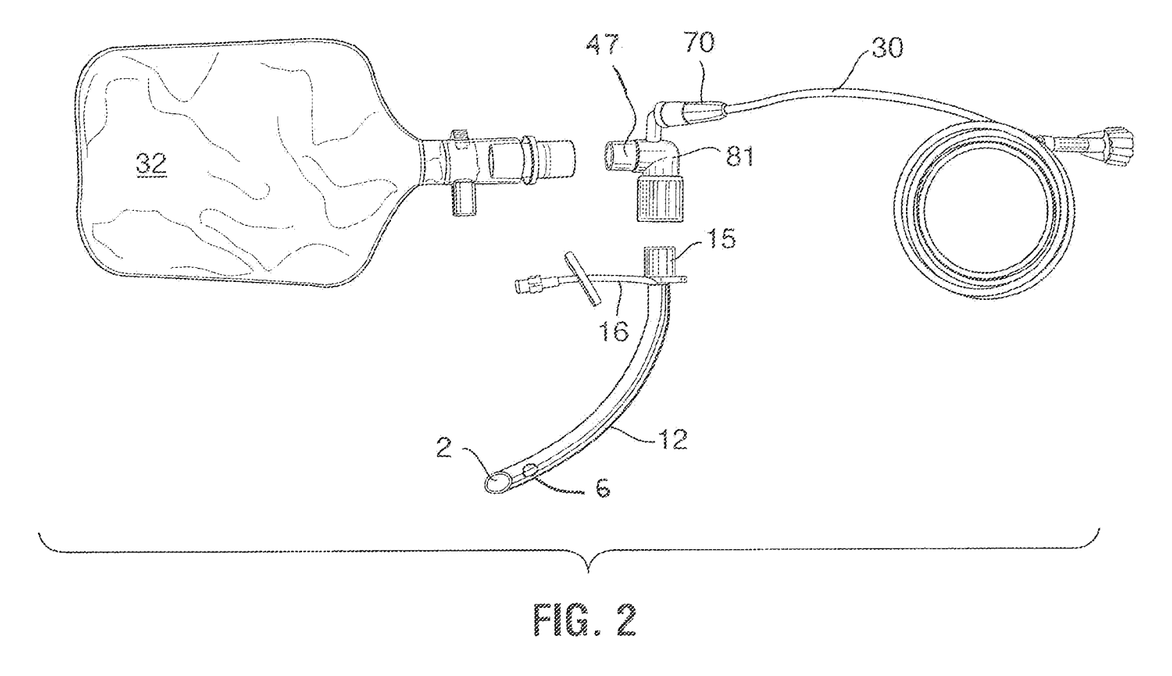
FIG. 2 shows the endopharyngeal airway device, modified JACKSON-REES ambu bag and ventilation pump tube before assembly.
Figure 3:
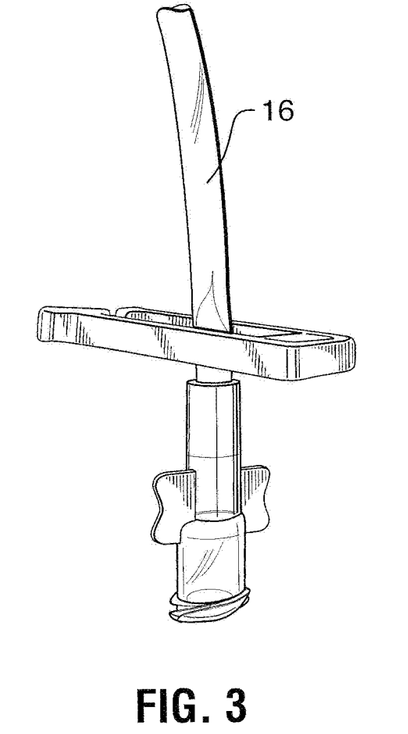
FIG. 3 is a perspective enlarged view of the port to end tidal CO2 monitor.
Figure 4:
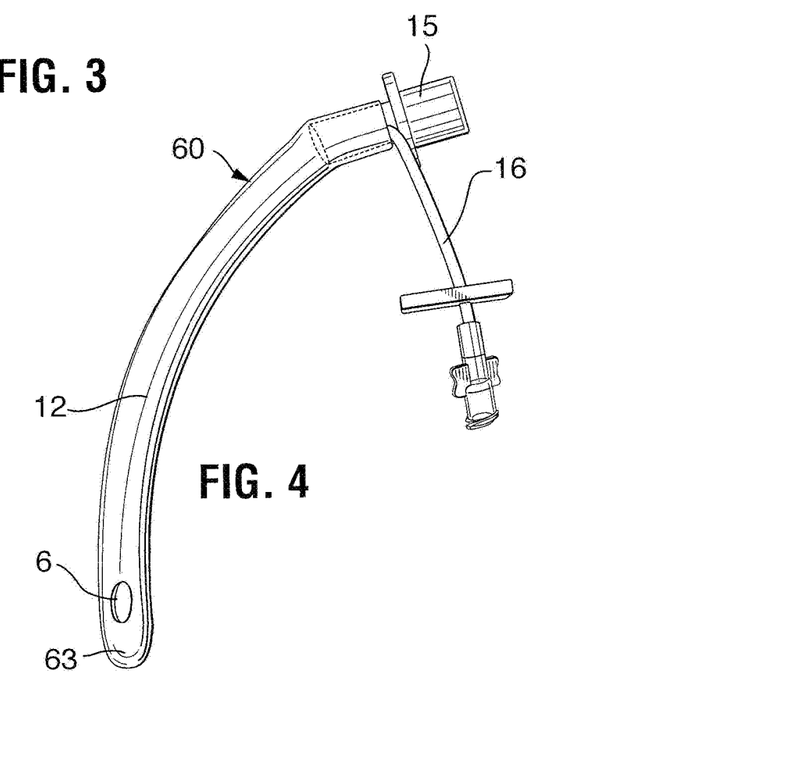
FIG. 4 is perspective view showing the endopharyngeal airway without various anesthesiology applications attached at the adaptor of the proximal end of the nasal tube.
Figure 6:
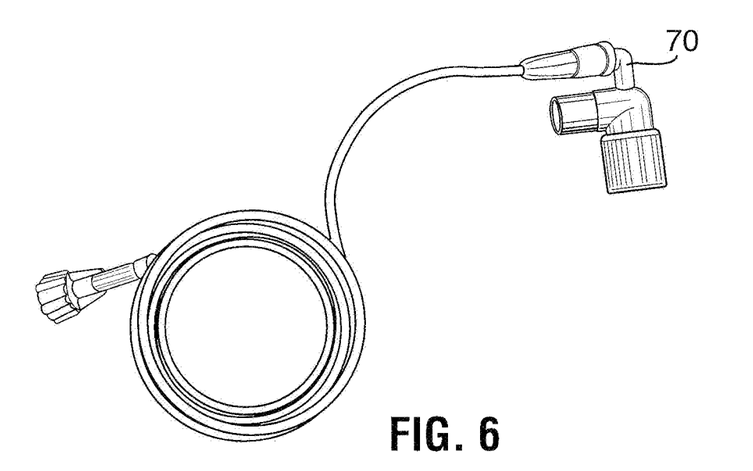
FIG. 6 is a perspective view of the ventilation pump tube with its female and male fitting adaptor parts.
Figure 7:
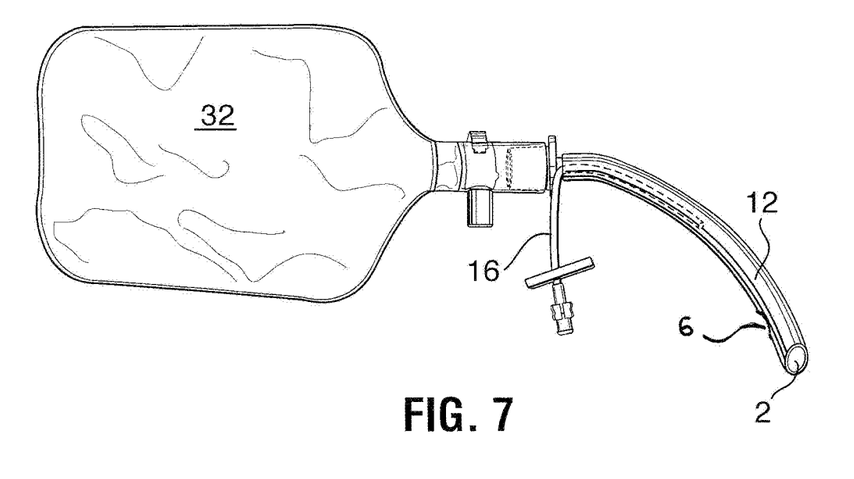
FIG. 7 is a perspective view of the modified JACKSON-REES ambu bag attached directly to the endopharyngeal nasal tube via its female fitting part.
Figure 8:
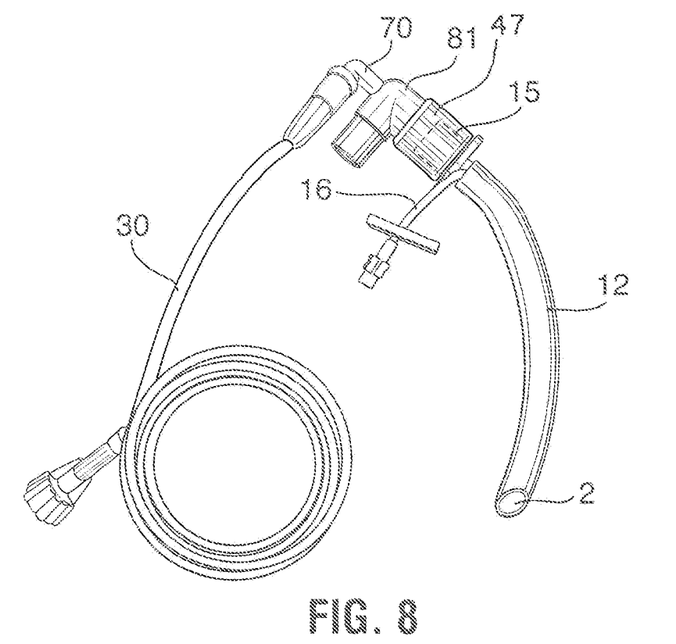
FIG. 8 is a perspective view of only the ventilation pump tube connected directly to the endopharyngeal nasal tube.

The air delivery assembly 61 generally includes adapters for cooperatively engaging and providing an air tight seal with a male fitting part of the adaptor 15 that is made to be quickly and easily wedged into the female fitting of multiple devices. The ventilation pump tube 30 is connected to the universal adaptor 81 by an air-tight, friction coupling between the nipple 70 which extends from the universal adaptor 81 and the proximal end of the ventilation pump tube 30. Once the ventilation pump tube 30 is joined with the universal adaptor 81, the universal adaptor can attach to the male fitting part of the adaptor 15. The modified JACKSON-REES ambu bag 32 includes a side port 22 and can either directly connect to the male fitting part of the adaptor 15 or connect to the universal adaptor's 81 male fitting part 47 and then be attached to the male fitting part of the adaptor 15.

Figure 9:
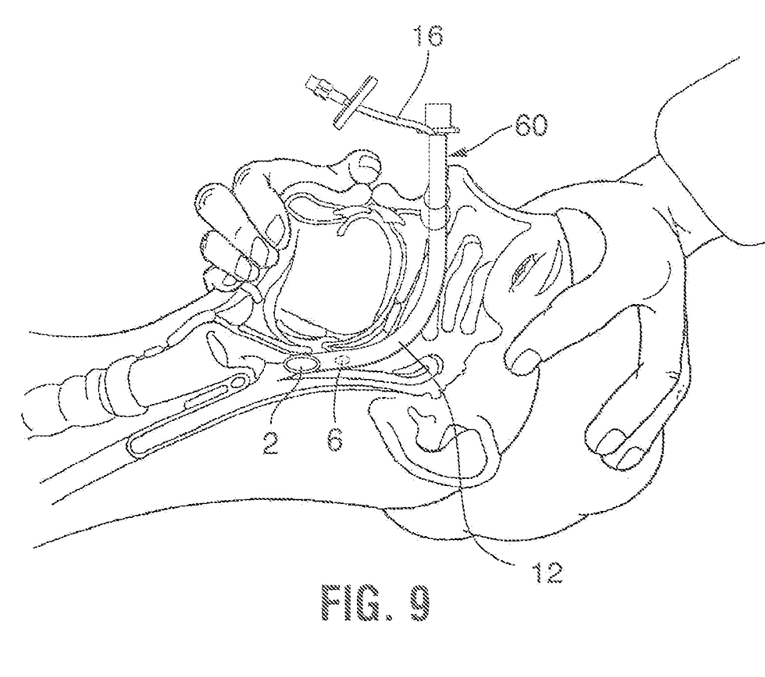
FIG. 9 is a perspective sectional view showing the endopharyngeal airway device inserted into the nostril of the patient for passage to the posterior pharynx.
Figure 10:
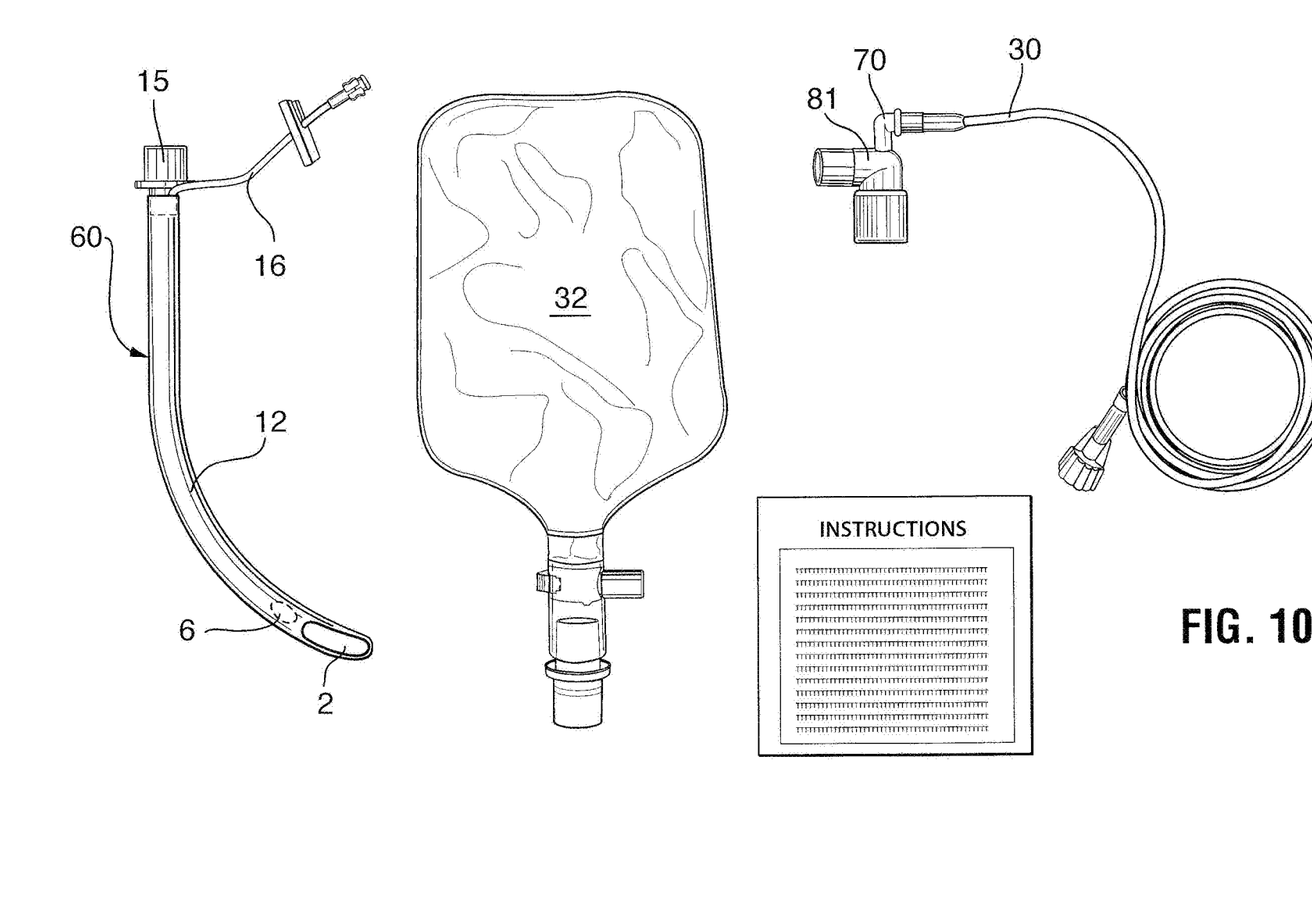
FIG. 10 is a perspective view of the operative elements of a ventilation kit including the endopharyngeal nasal tube.
Figure 11:
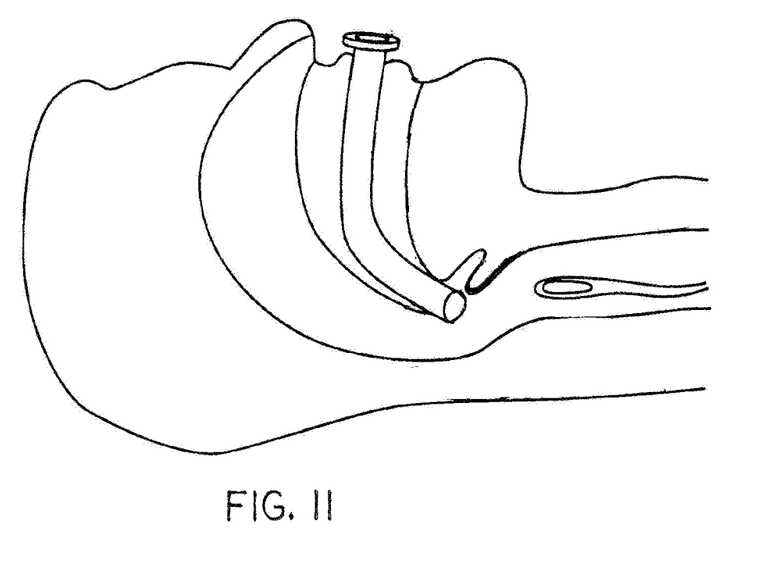
FIG. 11 is a perspective view of a conventional oropharyngeal airway tube positioned in the pharynx of a patient undergoing anesthesia.
Figure 12:
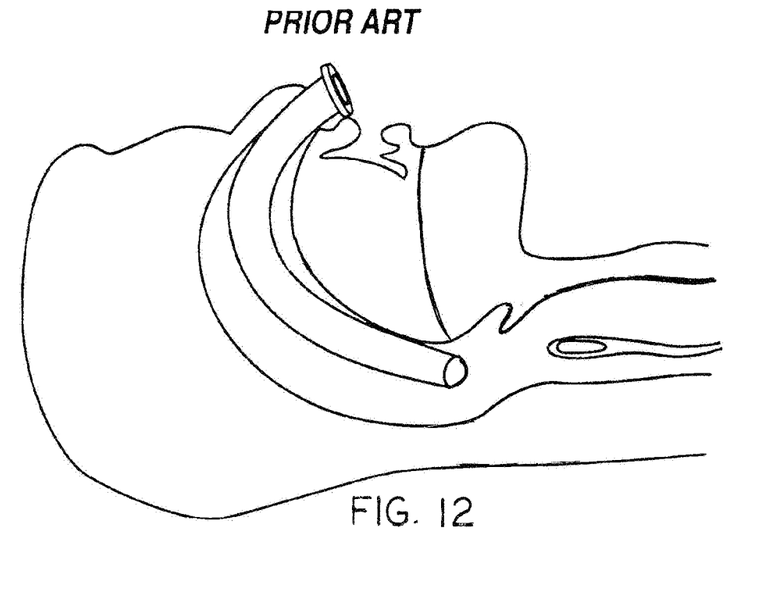
FIG. 12 is a perspective view of a conventional nasopharyngeal airway tube positioned in the pharynx of a patient undergoing anesthesia.

As shown in FIG. 9, the method of using the respiratory ventilation device 8 involves placing the patient in a face up prone position with the head slightly back to make certain the airway of the patient is open. Neosynephrine nasal spray is used in the least obstructed nares and a tube size is selected by measuring from the tip of the patients nose to their earlobe or angle of jaw. The respiratory ventilation device 8 is then lubricated with a lubricating gel and inserted by its distal end 63 into the least obstructed nostril of a patient and pushed downward until completely inserted and the distal end 63 is positioned posterior to the pharynx. Next, necessary accessories for the procedure such as the modified JACKSON-REES ambu bag 32 or ventilation pump tube 30 can be attached to the endopharyngeal nasal tube 60 via the adaptors. When using the modified JACKSON-REESE ambu bag 32 for assisted ventilation, the medical practitioner squeezes the ambu bag 32 to discharge a wave of air into the nasal passageway and lungs of the patient. The mouth of the patient may be held shut during the squeezing action and then allowed to open during the exhaling of the air. The delivery of the positive pressure air causes the periglottic space to expand as well as opening the larynx to facilitate pulmonary exchange of air. The medical practitioner can then squeeze the modified JACKSON-REESE ambu bag 32 in synchronization with the inspiratory phase allowing sufficient time for exhalation by the patient Referring now to the drawings and more particularly to FIG. 10, there is illustrated a ventilation respiratory ventilation device, which is constructed in accordance with another preferred embodiment of the present invention. The ventilation respiratory ventilation device is utilized to ventilate a medical patient. The respiratory ventilation device generally includes a storage container that holds all the operative elements of the device for easy in access and storage. In this regard, the container has a sufficient internal volume to hold the operative elements which include the endopharyngeal nasal tube, a modified JACKSON-REES ambu bag for assisted ventilation, a ventilation pump tube, and a set of instructions. The device contains a single-lumen endopharyngeal nasal tube with an eye shaped opening at its distal end and a cylindrical proximal end. Attached to the distal end is a flexible nasal ventilation tube made of a latex-free, non-toxic material. A small eye opening (commonly referred to as a Murphy eye) is disposed near the distal end and functions to allow the continued flow of air in the case that the distal end is blocked by body tissue. The ventilation pump tube is an elongated hollow tube having a female part threaded or friction fit first connector disposed at its distal end and a tight fitting sleeve second connector disposed at its proximal end. The first connector and the sleeve connector are both endotracheal tube connectors to permit one of them, to be quickly connected to the air bag and to permit the nasal tube end connector to be easily and quickly wedged into the proximal end of the nasal tube. Contiguous to the distal end of the nasal tube is an end-tidal $CO_2$ monitoring port (ETCO2) 16. The carbon dioxide port and/or quick disconnect coupling adapter can be integrally molded as part of the adapter which can be molded as part of the nasal tube.

The foregoing detailed description is given primarily for clearness of understanding and no unnecessary limitations are to be understood therefrom, for modification will become obvious to those skilled in the art upon reading this disclosure and may be made upon departing from the spirit of the invention and scope of the appended claims. Accordingly, this invention is not intended to be limited by the specific exemplification presented herein above. Rather, what is intended to be covered is within the spirit and scope of the appended claims.

I claim:

1. An endopharyngeal airway device for ventilating a patient consisting of:
   a single-lumen endopharyngeal nasal ventilation tube including an opening at a tapered distal end and an oblong opening in a sidewall spaced apart a selected distance from said tapered distal end;
   an endopharyngeal nasal tube adaptor having a distal male end for removable cooperative engagement with a proximate end of said single-lumen endopharyngeal nasal ventilation tube and a portion of a tube extending from a tidal CO2 monitoring port;
   said endopharyngeal nasal tube adaptor having an opposing male end in removable cooperative engagement with a sleeve of a universal adapter removably connecting to a positive pressure JACKSON-REES ambu-bag; and
   said positive pressure JACKSON-REES ambu-bag connecting to said universal adapter is configured to allow for controlled air flow to the patient during a procedure; and
   said universal adapter including a nipple for connecting to a ventilation pump tube in flow communication with a respiratory ventilation pump.

2. A portable endopharyngeal airway device for ventilating a patient consisting of:
   a single-lumen endopharyngeal nasal ventilation tube including an opening at a tapered distal end and an oblong opening in a sidewall spaced apart a selected distance from said tapered distal end;
   an endopharyngeal nasal ventilation tube adaptor having a distal male end for removable cooperative engagement with a proximate end of said single-lumen endopharyngeal nasal ventilation tube and a portion of a tube extending from a tidal CO2 monitoring port;
   said endopharyngeal nasal tube adaptor having an opposing male end in removable cooperative engagement with a sleeve of a universal adapter removably connecting to a positive pressure JACKSON-REES ambu-bag; and
   said positive pressure JACKSON-REES ambu-bag allows for controlled air flow to the patient during a procedure.

3. An endopharyngeal airway kit for ventilating a patient consisting of:
   a single-lumen endopharyngeal nasal ventilation tube including an opening at a tapered distal end and an oblong opening in a sidewall spaced apart a selected distance from said tapered distal end;
   an endopharyngeal nasal tube adaptor having a distal male end for removable cooperative engagement with a proximate end of said single-lumen endopharyngeal nasal ventilation tube and a portion of a tube extending from an end-tidal carbon dioxide monitoring port;
   a clamp for shutting off said tube extending from said end-tidal carbon dioxide monitoring port;
   said endopharyngeal nasal tube adaptor having an opposing male end in removable cooperative engagement with a sleeve of a universal adapter removably connecting to a positive pressure JACKSON-REES ambu-bag;
   said universal adapter including a nipple connecting to a ventilation pump tube in flow communication with a respiratory ventilation pump; and
   said positive pressure JACKSON-REES ambu-bag, and said respiratory ventilation pump allowing for controlled air flow to the patient during a procedure.

\* \* \* \* \*